(12) United States Patent
Wasielewski

(10) Patent No.: US 7,591,854 B2
(45) Date of Patent: *Sep. 22, 2009

(54) APPARATUS, SYSTEM AND METHOD FOR INTRAOPERATIVE PERFORMANCE ANALYSIS DURING JOINT ARTHROPLASTY

(75) Inventor: Ray C. Wasielewski, Westerville, OH (US)

(73) Assignee: Depuy Products, Inc., Warsaw, IN (US)

( * ) Notice: Subject to any disclaimer, the term of this patent is extended or adjusted under 35 U.S.C. 154(b) by 593 days.

This patent is subject to a terminal disclaimer.

(21) Appl. No.: 10/667,763

(22) Filed: Sep. 22, 2003

(65) Prior Publication Data
US 2004/0064191 A1 Apr. 1, 2004

Related U.S. Application Data

(60) Provisional application No. 60/414,794, filed on Sep. 30, 2002.

(51) Int. Cl.
*A61F 2/38* (2006.01)
(52) U.S. Cl. ............ 623/20.14; 623/914; 600/377
(58) Field of Classification Search ... 623/20.14–20.36, 623/914; 600/587, 595, 377; 606/88, 86, 606/89
See application file for complete search history.

(56) References Cited

U.S. PATENT DOCUMENTS

| | | | |
|---|---|---|---|
| 4,856,993 A | 8/1989 | Maness et al. | |
| 5,033,291 A | 7/1991 | Podoloff et al. | |
| 5,197,488 A * | 3/1993 | Kovacevic | 600/595 |
| 5,326,363 A | 7/1994 | Aikins | |
| 5,360,016 A | 11/1994 | Kovacevic | |
| 5,425,775 A | 6/1995 | Kovacevic et al. | |
| 5,470,354 A * | 11/1995 | Hershberger et al. | 128/898 |
| 5,496,352 A | 3/1996 | Renger | |
| 5,609,643 A * | 3/1997 | Colleran et al. | 623/20.29 |
| 5,733,292 A * | 3/1998 | Gustilo et al. | 606/88 |
| 5,840,047 A | 11/1998 | Stedham | |
| 5,871,541 A * | 2/1999 | Gerber | 623/20.29 |
| 6,174,294 B1 | 1/2001 | Crabb et al. | |

OTHER PUBLICATIONS

Behrens, Fred M.D., et al, "Bendign Stiffness of Unilateral and Bilateral Fixator Frames," Clinical Orthopaedics and Related Research (Sep. 1983), p. 103.-110.

Markolf, Keith L., Ph.D., et al, "In Vitro Measurement of Bone-Acrylic Interface Pressure During Femoral Component Insertion," Clinical Orthopaedics and Related Research (Nov.-Dec. 1976), p. 60-66.

(Continued)

*Primary Examiner*—Pedro Philogene

(57) ABSTRACT

An instrumented joint trial has a polymer layer defining a curved contoured articulating surface. A curved contoured sensor array is positioned below the polymer layer. Other components of the joint trial, such as a body with a proximal curved contoured surface, are positioned below the sensor array. The device can be made by forming a sheet of the polymer over the curved contoured surface of the joint trial body and then adhering the sensor array to one curved contoured surface of the formed polymer. The sensor array conforms to the shape of the formed polymer layer. The system includes a mating joint trial. The device may be used by temporarily attaching the joint trial to a resected portion of bone and then articulating the joint with the instrumented trial in place.

27 Claims, 9 Drawing Sheets

OTHER PUBLICATIONS

English, T.A., et al, "In Vivo Records of Hip Loads Using a Femoral Implant with Telemetric Output (A Preliminary Report)," Journal Biomedical Engineering (Apr. 1979), vol. 1 (No. 2), p. 111-115.

Oh, Indong, M.D., et al, "Proximal Strain Distribution in the Loaded Femur," The Journal of Bone and Joint Surgery (Jan. 1978), vol. 60A (No. 1), p. 75-85.

Takahashi, Toshiaki et al, "Soft Tissue Balancing with Pressure Distribution During Total Knee Arthroplasty," The Journal of Bone and Joint Surgery (Mar. 1997), p. 235-239.

Davy, D.T., et al, "Telemetric Force Measurements Across the Hip after Total Arthroplasty," The Journal of Bone and Joint Surgery (Jan. 1988), vol. 70A (No. 1), p. 45-50.

Gupta, Sushi K., M.D., et al, "Use of Piezoelectric Film Sensor for Monitoring Vascular Grafts," The American Journal of Surgery (Aug. 1990), p. 182-186.

McDermott, A.G.P., M.D., et al, "A New Method to Measure Intraosseous Pressures," Clinical Orthopaedics and Related Research (Jul. 1986), p. 25-27.

Mann, R.W., et al, "Rehabilitation Implications of In Vivo Hip Pressure Measurements," Proceedings of the Ninth Annual Conference on Rehabilitation Technology (Jun. 23-26, 1986), Association for the Advancement of Rehabilitation Technology (Minneapolis, Minnesota (Copyright 1986)).

Hodge, W.A., M.D., et al, "Contact Pressures from an Instrumented Hip Endoprosthesis," The Journal of Bone and Joint Surgery Incorporated (Oct. 1989), vol. 71A (No. 9), p. 1378-1386.

Wasielewski, Ray C. "Declaration" unpublished, dated Aug. 22, 2007.

Carlson, Charles E., et al, "A Radio Telemetry Device for Monitoring Cartilage Surface Pressures in the Human Hip," IEEE Transactions on Biomedical Engineering (Jul. 1974) vol. BME-21, No. 4.

* cited by examiner

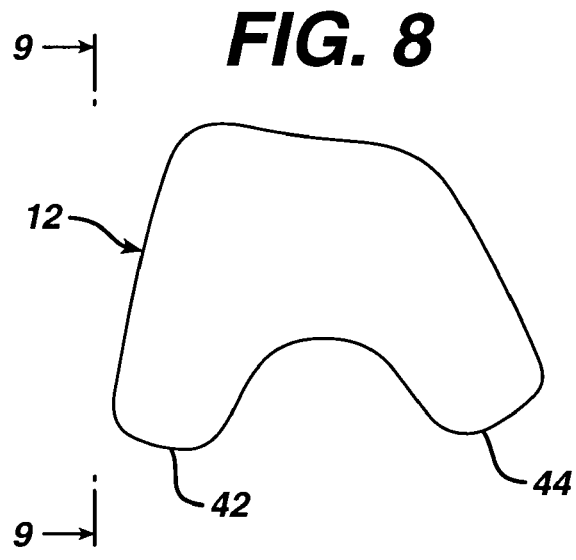
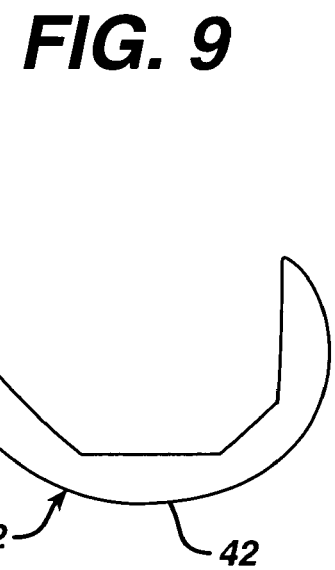
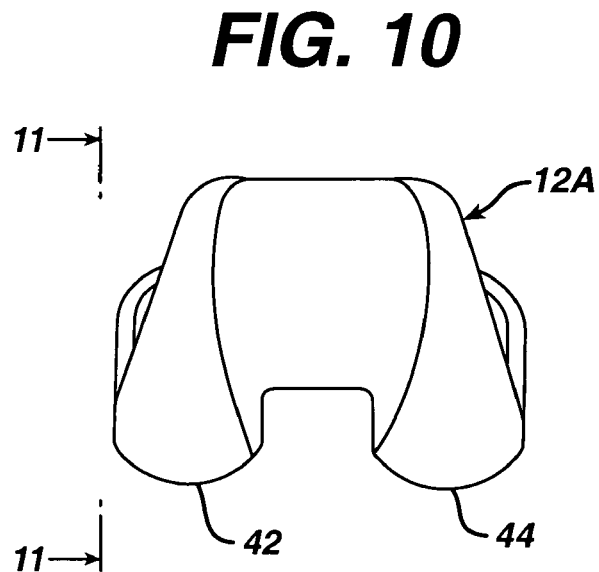
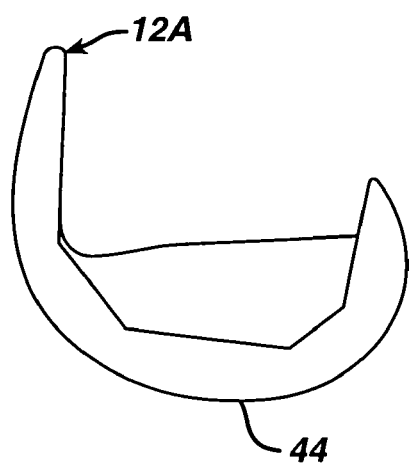

APPARATUS, SYSTEM AND METHOD FOR INTRAOPERATIVE PERFORMANCE ANALYSIS DURING JOINT ARTHROPLASTY

This application claims the benefit of U.S. Provisional Application No. 60/414,794, filed Sep. 30, 2002.

BACKGROUND OF THE INVENTION

The present invention relates to an apparatus, system and method for intraoperative performance analysis during joint arthroplasty.

In total joint replacement or arthroplasty, bone orientation, selection of prosthetic joint components and soft tissue balancing are critical to the success of the procedure. Considering, for example, total knee arthroplasty, one or more cutting jigs are used to ensure that the distal end of the femur and proximal end of the tibia are cut in an orientation that will properly align the patient's bones. After the bones are cut or resected, prosthetic components are fixed to the femur, tibia and patella to define the prosthetic knee joint.

A successful joint replacement or arthroplasty procedure results, in part, from selection of prosthetic joint components that are dimensioned and positioned to closely approximate or replicate the geometry and functional characteristics of a natural, healthy joint. Typically, the component selection process includes a pre-operative analysis of joint images. A valuable intraoperative adjunct to image analysis is the temporary fixation of one or more provisional components to a bone or bones of interest at a stage of the arthroplasty procedure prior to permanent fixation of the prosthetic joint. The provisional components are intended to mimic certain aspects of the permanent prosthetic joint in order for a surgeon to validate measurements and to test or "try-out" several different possible component sizes and configurations. Hence, provisional components are aptly known as "trials."

In total knee arthroplasty, femoral and tibial trials are used to assist a surgeon in assessing the correct resection and alignment prior to implantation of the femoral and tibial portions of the artificial knee. A surgeon uses a tibial tray trial before fixation of the final implant to determine the tibial implant size, to check that and correct bone cut and reaming has occurred, to assess alignment and to ensure correct tibial component thickness prior to implanting the tibial components. The surgeon uses the femoral trial for similar purposes.

Successful knee arthroplasty also requires an analysis of the soft tissue supporting the knee. The knee is held together by a number of ligaments, muscles and tendons. Generally, the surgeon must ensure that these ligaments, muscles and tendons will be properly balanced with the prosthetic elements in place. A properly balanced knee joint will demonstrate balanced ligament tension in both extension and flexion. If the ligaments and tendons around the knee are not properly balanced, the result may be poor performance, localized high stress on the prosthetic components and undesirable wear on the prosthetic components.

Commonly, surgeons assess ligament tension through a subjective process using spacer blocks and mechanical tensioners. If the surgeon senses that either the medial or lateral side is under excess tension, the surgeon relieves the excess tension by releasing a part of either the medial or lateral collateral ligament. However, the surgeon does not necessarily obtain the feedback necessary during ligament release to help assess whether the release is adequate throughout the range of motion; full range of motion information can only be obtained with the trial in place. In addition, the surgeon must be careful to avoid over-release of the collateral ligaments, since the surgeon cannot undo the release.

In some cases it is preferable to retain the native posterior cruciate ligment. Some prosthetic knees are designed to be used with the posterior cruciate ligament in place along with the prosthetic device. In these procedures, surgeons assess tension in the posterior cruciate ligament with femoral and tibial trials in place on the resected surfaces of the femur and tibia. Too much tension could result in premature wear of the prosthetic components, and too little tension can make the knee unstable. Surgeons generally release some of the fibrous attachments between the posterior cruciate ligament and the tibia until they are satisfied with the degree of tension in the ligament. The current intraoperative posterior cruciate ligament release procedure relies heavily on the surgeon's experience and subjective observations, rather than on objective intraoperative measurement of ligament tension.

SUMMARY OF THE INVENTION

In one aspect, the present invention provides an instrumented prosthetic knee trial comprising an articulating surface, a polymer layer, a body and a sensor array. The polymer layer is located at the articulating surface. The body has a curved contoured surface. The sensor array is between the polymer layer and the curved contoured surface of the body. The sensor array has a curved contour substantially following the curved contour of at least part of curved contoured surface of the body. The sensor array is capable of generating a signal in response to pressure. The polymer layer has a curved contour substantially following the curved contour of the sensor array. The polymer layer overlies substantially all of the sensor array.

In another aspect, the present invention provides a knee joint tension sensor device comprising a polymer layer and a sensor array. The sensor array is secured to the polymer layer. The polymer layer and the sensor array both have a curved contour. The sensor array is capable of generating a signal in response to pressure.

In another aspect, the present invention provides a system for balancing soft tissue intraoperatively during knee joint arthroplasty. The system includes a first joint trial having a curved convex articulating surface and a second joint trial having a curved concave articulating surface for receiving the convex articulating surface of the first joint trial. The second joint trial includes a polymer layer at the articulating surface, a sensor array and a body. The sensor array is below the polymer layer. The sensor array has a curved convex undersurface contour substantially following the curved concave contour of the articulating surface. The sensor array is capable of generating a signal in response to pressure. The body is below the sensor array, and has a curved concave surface adjacent to the sensor array.

In another aspect, the present invention provides a method of making an instrumented prosthetic knee trial. A curved contoured forming surface is provided, along with a conformable sensor array and a polymer material. The polymer material is formed over the curved contoured forming surface so that the polymer material has a curved contoured surface that substantially mates with the curved contoured forming surface. The forming can be accomplished by vacuum forming. The formed polymer material and conformable sensor array are assembled so that the conformable sensor array is positioned against the curved contoured surface of the polymer material. The conformable sensor array conforms substantially to the curved contoured surface of the polymer material.

In another aspect, the present invention provides a method of balancing soft tissue during knee joint arthroplasty. A first joint trial having a curved convex articular surface is provided, along with an instrumented second joint trial. The instrumented second joint trial has a curved concave articulating surface for receiving the convex articulating surface of the first joint trial. The second joint trial includes a curved concave protective layer at the articulating surface, a sensor array and a body. The sensor array is below the protective layer. The sensor array has a curved concave contour substantially following the curved concave contour of the articulating surface of the second joint trial, and is capable of generating a signal in response to pressure. The body is below the sensor array. The body has a curved concave surface adjacent to the sensor array. The method further comprises resecting adjacent portions of two bones, placing the first joint trial on one of the resected bones and the second joint trial on the second resected bone. The surgeon then flexes the bones about the first and second joint trials so that portions of the first joint trial bear against contact portions of the protective layer.

In another aspect, the present invention provides a method of instructing surgeons in the art of knee joint arthroplasty. A first joint trial having a curved convex articular surface is provided, along with an instrumented second joint trial. The instrumented second joint trial has a curved concave articulating surface for receiving the convex articulating surface of the first joint trial. The second joint trial includes a curved concave protective layer at the articulating surface, a sensor array and a body. The sensor array is below the protective layer. The sensor array has a curved concave top surface contour substantially following the curved concave contour of the articulating surface of the second joint trial, and is capable of generating a signal in response to pressure. The body is below the sensor array. The body has a curved concave top surface adjacent to the sensor array. The method further comprises resecting adjacent portions of two bones, placing the first joint trial on one of the resected bones and the second joint trial on the second resected bone. The surgeon then flexes the bones about the first and second joint trials so that portions of the first joint trial bear against contact portions of the protective layer allowing for measurement of the forces between the trials.

In another aspect, the present invention provides a system for balancing soft tissue intraoperatively during knee joint arthroplasty. The system comprises a body having a curved concave surface, a conformable sensor array, and a preformed protective cover having a curved concave surface and a curved convex surface.

BRIEF DESCRIPTION OF THE DRAWINGS

In the accompanying drawings, prosthetic joint trials are illustrated, with like reference numbers used for like parts in all embodiments.

FIG. 8 is a front elevation of a typical femoral trial;

FIG. 9 is a side elevation of the femoral trial of FIG. 8, taken along line 9-9 of FIG. 8;

FIG. 10 is a front elevation of another typical femoral trial;

FIG. 11 is a side elevation of the femoral trial of FIG. 10, taken along line 11-11 of FIG. 10;

DETAILED DESCRIPTION OF THE ILLUSTRATED EMBODIMENTS

Figure 5:
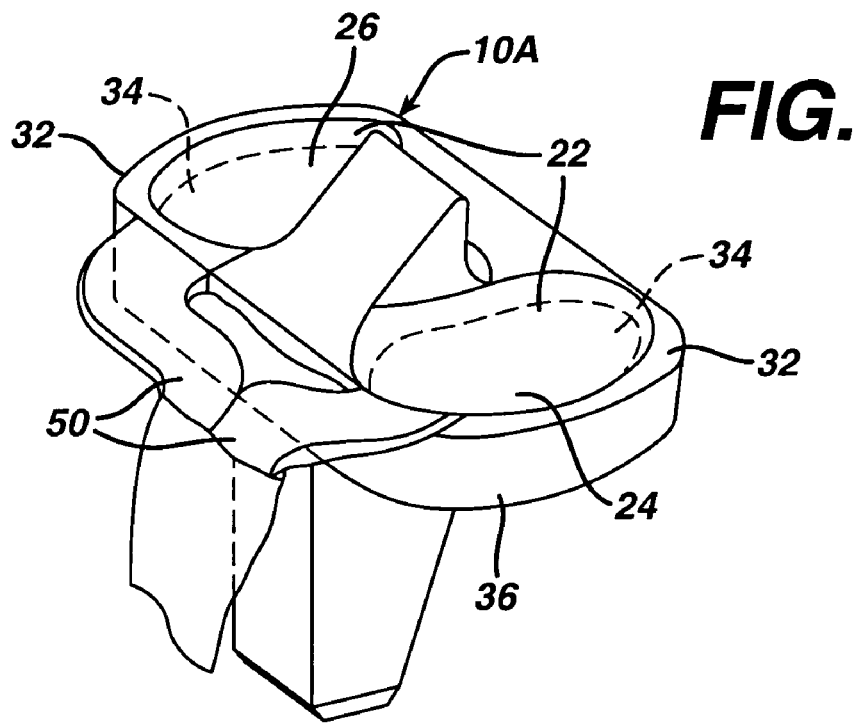
FIG. 5 is a perspective view of a second embodiment of an instrumented tibial insert trial.
Figure 6:
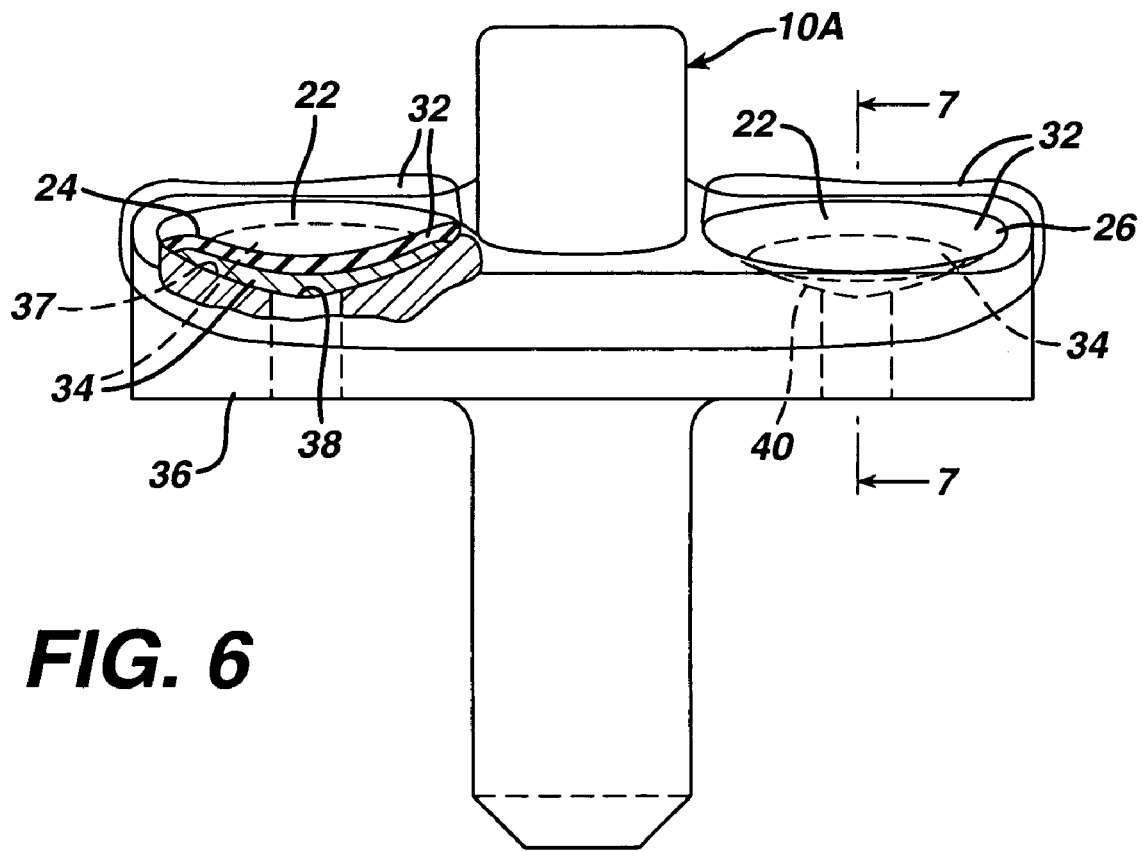
FIG. 6 is an elevation of the instrumented tibial insert trial of FIG. 5, shown in partial cross-section.
Figure 7:
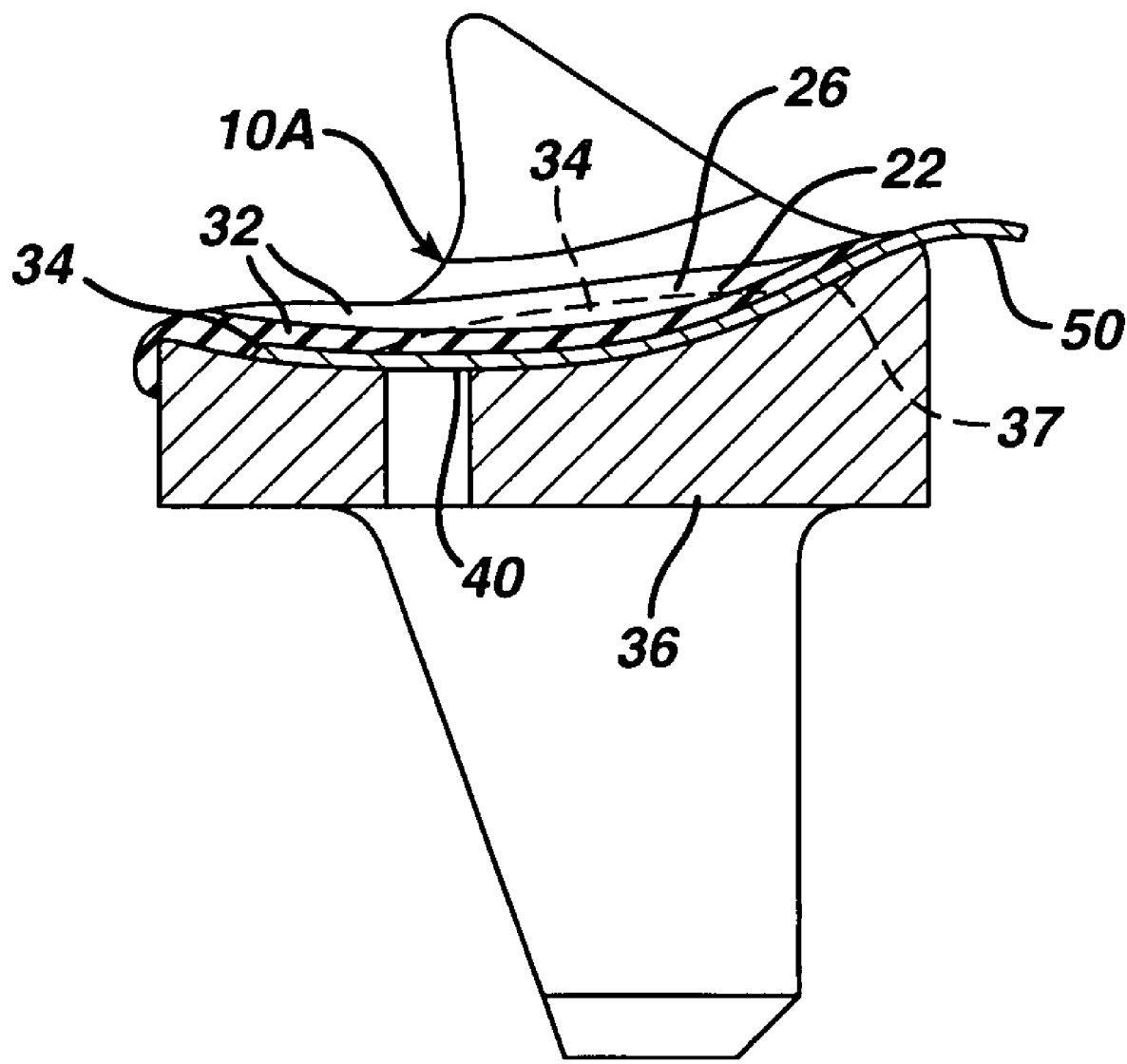
FIG. 7 is a cross-section of the instrumented tibial insert trial of FIGS. 5-6, taken along line 7-7 of FIG. 6.

The first embodiment of the invention, illustrated in FIGS. 1-4, comprises an instrumented tibial trial insert 10. Another embodiment of an instrumented tibial trial insert is illustrated in FIGS. 5-7 at 10A. An embodiment of a joint tension sensor device is illustrated at 10B in FIGS. 15-17.

Figure 12:
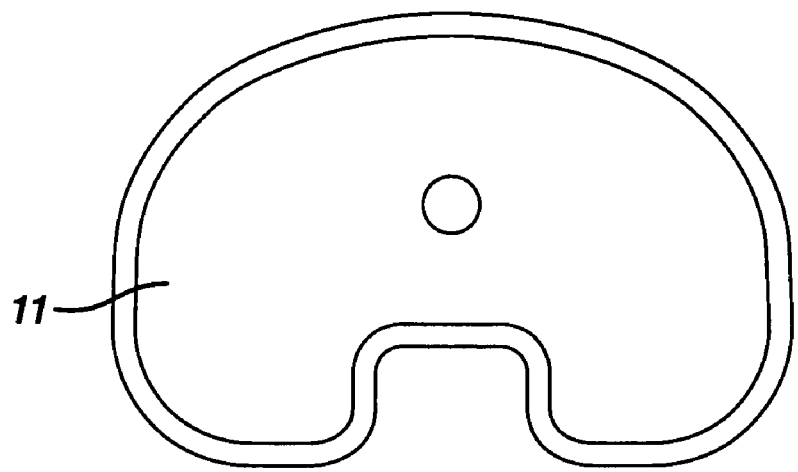
FIG. 12 is a top plan view of a typical tibial tray trial.
Figure 13:
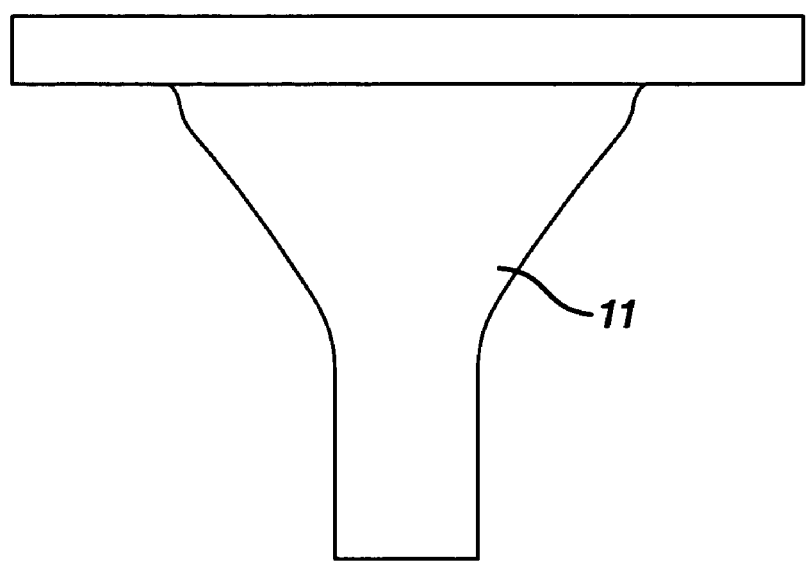
FIG. 13 is a front elevation of the tibial tray trial and stem of FIG. 12.

Each illustrated tibial trial insert 10, 10A, 10B is part of a tibial trial that also includes a tibial trial tray and stem, such as that shown at 11 in FIGS. 12-13. The entire tibial trial assembly is designated 13 in FIGS. 1 and 4. For a tibial trial insert like that shown in FIGS. 5-7, the tibial tray and stem would have a different design than for the design shown in FIGS. 12-13. Each tibial trial is part of a trial system that also includes a femoral trial, examples of which are illustrated in FIGS. 8-11 as 12 and 12A. The femoral trials could be one-piece or multiple piece parts of the system or kit. A surgical kit would typically include several different sizes of both tibial trials and femoral trials.

The surgeon uses the trials 11, 12, 12A, 13 (see FIGS. 4, 8-13) as provisional joint components, removably attaching them to the resected tibia and femur during the arthroplasty prior to permanent fixation of the prosthetic joint. It should be understood that there are a great variety of designs for tibial and femoral trials, and that the illustrated shapes, sizes and construction (e.g. modular versus integral) for all the elements are provided by way of example only; the present invention is not limited to any shape, size, material, or construction of any element unless expressly set forth in the claims.

Figure 4:
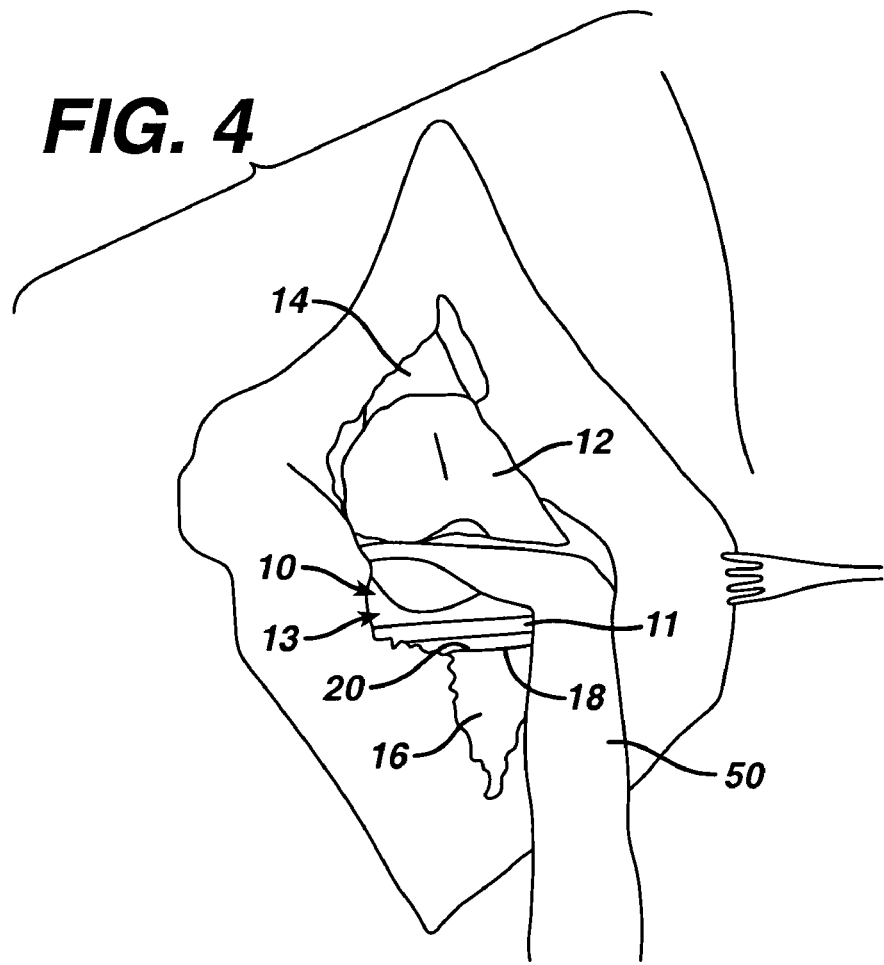
FIG. 4 is a diagrammatic view of the instrumented tibial trial of FIGS. 1-4, together with a femoral trial, in position on the resected surfaces of a patient.

FIG. 4 illustrates two such prosthetic trials 12, 13 in place on a femur 14 and tibia 16. The trial components 12, 13 are intended to mimic certain aspects of the permanent prosthetic tibial and femoral joint elements in order for a surgeon to validate measurements and to test or "try-out" several different possible component sizes and configurations.

As shown in FIG. 4, the illustrated instrumented tibial trial 13 includes a distal plate portion 18 for contacting the proximal plane 20 of the resected tibia 16. The instrumented tibial trial 13 also includes an articulating surface 22, shown in FIGS. 1-3, 5-7 and 15-17. In both embodiments illustrated in FIGS. 1-4 and 5-7, the articulating surface 22 is part of the instrumented tibial insert trial 10, 10A. Each articulating surface 22 has a curved contour with medial and lateral curved concave portions 24, 26 connected by a raised central portion 28 and surrounded by a raised outer edge 30.

Figure 2:
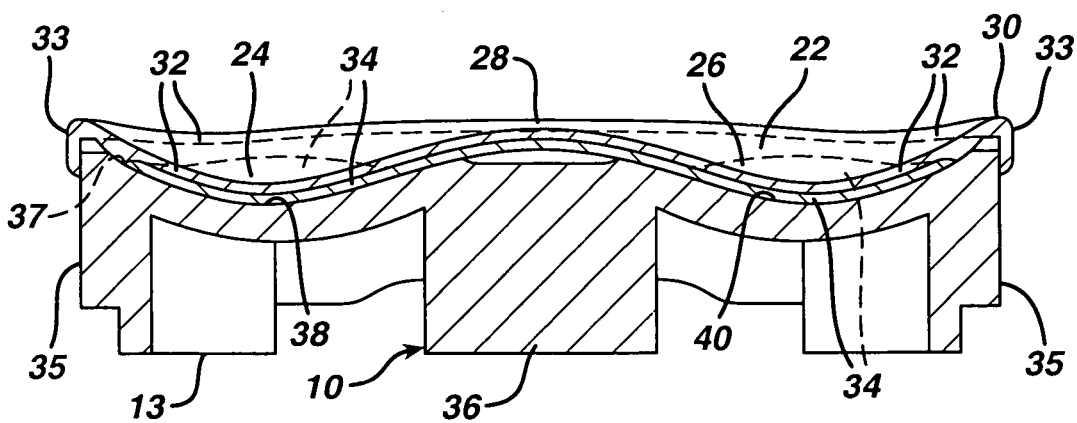
FIG. 2 is a cross-section of the instrumented tibial insert trial portion of the instrumented tibial trial of FIG. 1, taken along line 2-2 of FIG. 1.

The articulating surface 22 of the instrumented tibial trial 13 is defined by a polymer layer 32. The polymer layer 32 covers and protects a sensor array 34. The illustrated sensor array 34 has medial and lateral curved portions that rest upon complementary curved concave portions of a body 36. The illustrated sensor array 34 is concave on its proximal surface against the polymer layer 32 and convex on its distal surface against the tibial trial insert body. In other words, the sensor array 34 is sandwiched between surfaces of the polymer layer 32 and the body 36 of the tibial trial insert that have complementary curved contours. The sensor array is shaped to conform with the shapes of the surfaces above and below it. These curved contoured portions of the instrumented tibial trial are shaped to complement the shapes of the condylar portions at the distal end of the femoral trial, such as the curved condylar portions shown at 42, 44 in FIGS. 8-11. As shown in FIG. 2, the polymer layer 32 may include side edges 33 that provide an interference fit over the sides 35 of the body 36.

Generally, the polymer layer 32 should be capable of protecting the sensor array 34 from the stresses of the trialing process, be capable of being sterilized for use in surgery, and be capable of transferring stress to the sensor array 34 so that forces and pressure distributions and concentrations can be evaluated as discussed below. The polymer layer 32 in the illustrated embodiments comprises high density polyethylene. The illustrated polymer layer has a thickness of about 1/32 inch (about 0.8 mm), or slightly more, and can be formed from a sheet of polyethylene. A commercially available material may be used for the polymer layer 32. A suitable example is 0.020" HDPE sheet and 0.030" HDPE sheet material available from Eastech Plastics of Columbus, Ohio. It should be understood that the particular material and form of this material are identified for purposes of example only; the present invention is not limited to any particular polymer or any particular form of polymer unless expressly called for in the claims. For example, depending on the procedure used for making the tibial trial insert, materials such as low density polyethylene and polypropylene might be usable.

Figure 1:
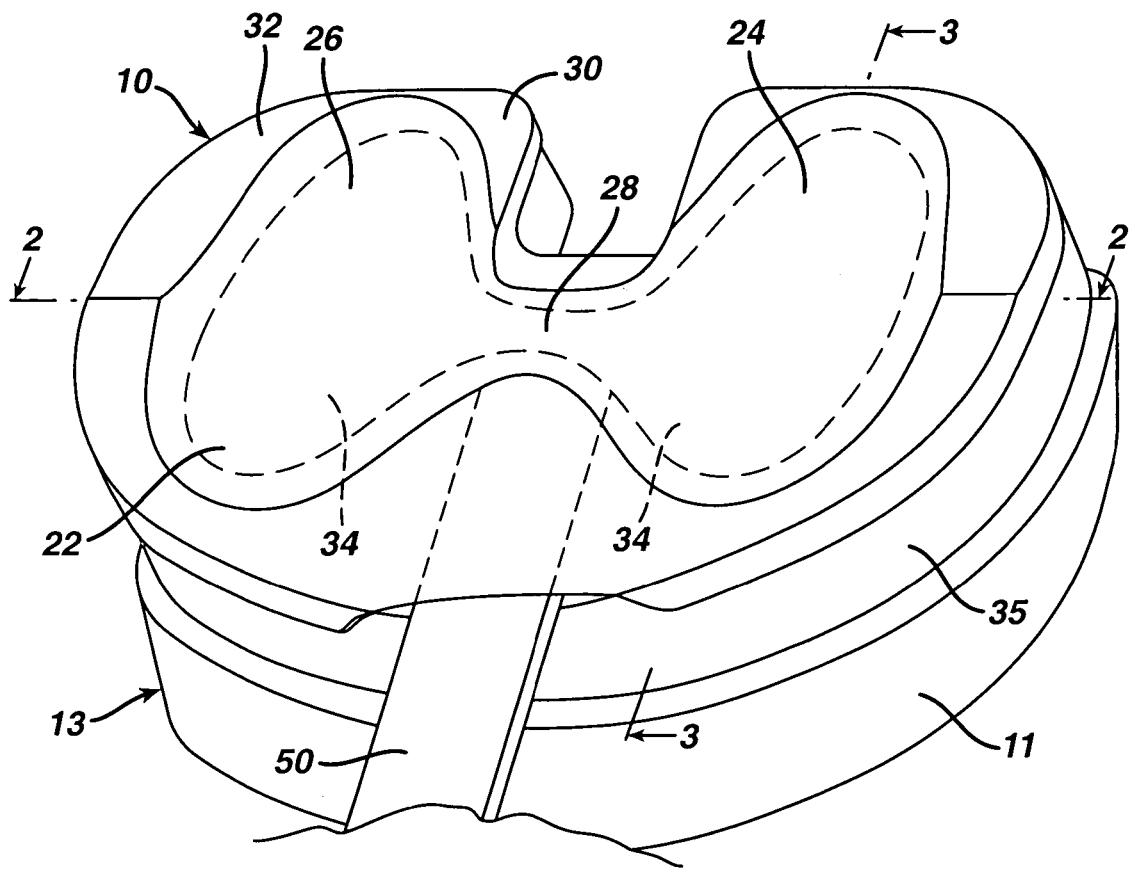
FIG. 1 is a perspective view of an instrumented tibial trial incorporating the principles of the present invention.

The sensor array 34 in the illustrated embodiments comprises a grid of pressure transducers, connected together to define a thin, flexible and conformable sheet. Two sensor arrays 34 could be provided, one for each of the medial and lateral curved concave portions 24, 26 of the articulating surface 22. Alternatively, a single butterfly-shaped sensor array could be provided, one wing for each of the medial and lateral curved concave portions 24, 26 of the articulating surface 22, as illustrated in FIG. 1. The pressure transducers produce a signal in response to pressure; in the illustrated embodiments, the sensor array 34 produces electrical signals, but the invention is not so limited unless expressly called for in the claims.

An illustrative sensor array 34 preferably has the following characteristics: it is thin (e.g 1.5 mm thick), usable over the range of anticipated pressures (e.g. 5 N/cm$^2$-200 N/cm$^2$), elastically comformable to the insert contour, and has the ability to be sterilized, particularly by conventional sterilization techniques. However, it should be understood that unless a particular characteristic is expressly called for in the claims, the invention is not intended to be limited to any particular characteristic.

The sensor array 34 preferably underlies the entire area of the articulating surface 22 that is designed to interface with the mating articulating surface of the femoral trial. It should be understood that the actual shape and dimensions for each sensor array will therefore vary with the design and size of the trials.

A suitable example of a commercially available sensor array 34 is available from novelElectronics Inc. of St. Paul Minn. (and novel gmbH of Munich, Germany, www.novel.de). It is identified by novel as part of the "pliance" system. Each pad has 128 pressure sensors, a thickness of about 1.5 mm, a total sensor area of 43×21.5 mm$^2$, an elasticity of greater than 2%, a sensitivity of less than 2 N/cm$^2$ and greater than 4 N/cm$^2$, and a usable pressure range of 5-200 N/cm$^2$. Two such pads may be used in each instrumented tibial trial insert 10, 10A, 10B. It should be understood that this particular sensor array and the above-identified characteristics of the sensor array are provided by way of example only; the present invention is not limited to this sensor array or these characteristics unless expressly called for in the claims. For example, it is expected that new materials and new products will become commercially available that could be used with the present invention; for example, a capacitive fabric could be usable.

It should be understood that the accompanying drawings are not drawn to scale. Typically, the sensor array may have a thickness on the order of 1.5 mm or less, for example, while the polymer layer may have a thickness of about 0.8 mm (1/32 inch), for example.

Figure 18:
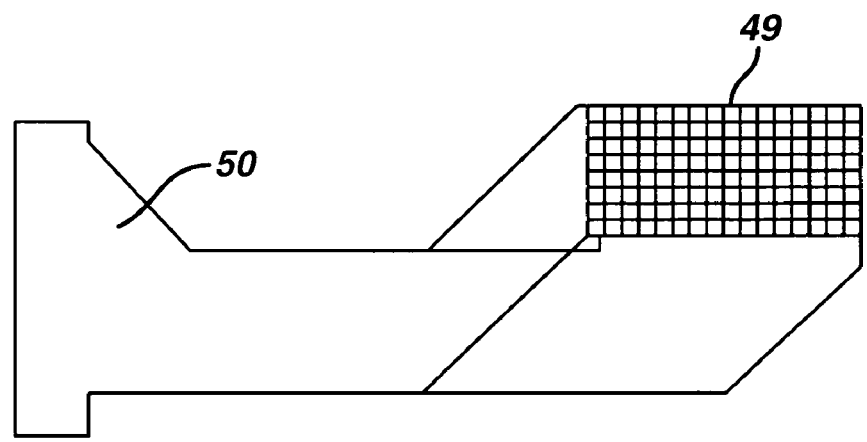
FIG. 18 is diagrammatic plan view of a sensor mat that can be used in the present invention, two of which can be joined with a polymer layer to form the joint tension sensor device of FIGS. 15-17, and two of which can be joined with a polymer layer and body to form an instrumented tibial insert trial as illustrated in FIGS. 1-11.

A diagrammatic representation of an example of a sensor mat 49 is shown in FIG. 18. Two such mats would be present in a sensor array 34 for a single tibial trial.

The body 36 of the prosthetic tibial trial may comprise a standard tibial insert trial, to be used with a standard corresponding tray trial, e.g. as shown at 11 in FIG. 4. The standard insert trial may have a standard proximal surface 37 with standard medial and lateral portions with concavely-curved contours, as shown at 38, 40 in FIGS. 2-3 and 6-7. Opposite the curved contours 38, 40 the tibial trial inset has a distal portion that is supported on the tibial tray trial 11. Generally, in prior designs, the proximal surface 37 of the body 36 would have been the articulating surface of the tibial trial.

The tibial trial insert body 36 may be made of standard materials, such as nylon, UHMWPE, acetal copolymer, polyethylene or polypropylene, for example, and the tray trial 11 may be made of standard material such as stainless steel. Such standard prosthetic tibial trial components are available from DePuy Orthopaedics, Inc. of Warsaw, Ind. under trademarks such as: LCS®, LCS® COMPLETE, PFC SIGMA, and PFC SIGMA RP. However, it should be understood that these commercial products are identified for purposes of illustration only; the invention is not limited to any particular product unless expressly called for in the claims.

Figure 3:
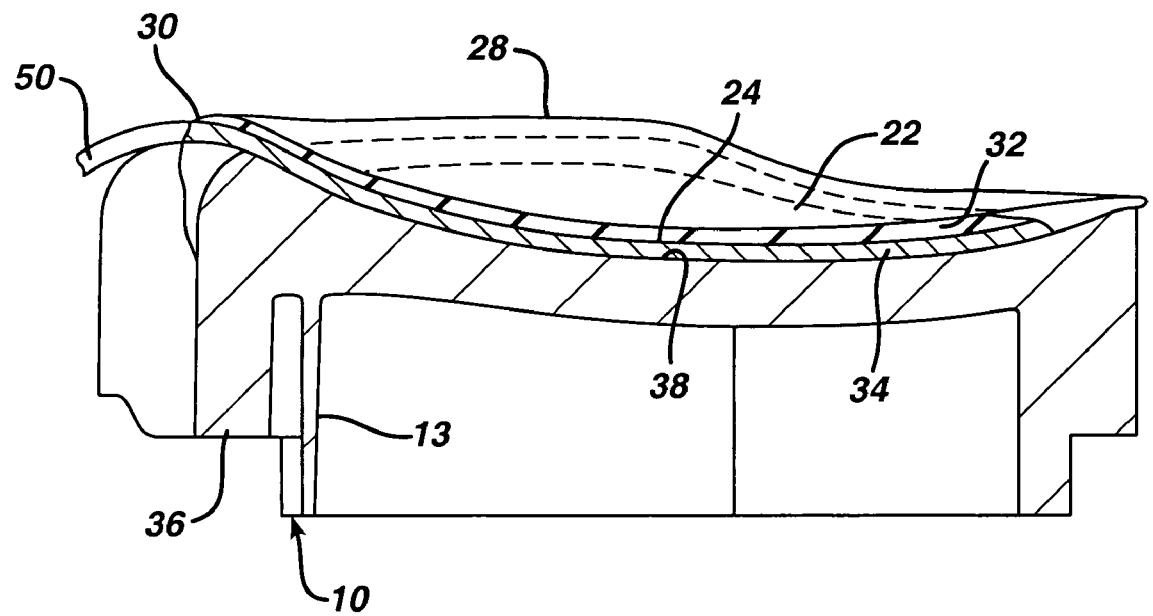
FIG. 3 is a cross-section of the instrumented tibial insert trial portion of the instrumented tibial trial of FIGS. 1-2, taken along line 3-3 of FIG. 1.

The designs, shapes, sizes and construction of the trials may vary from those shown in the embodiments of FIGS. 1-3. Other implant designs will typically have trials generally corresponding in shape and size to the implant components. For example, the tibial trial of the present invention may be shaped for use with cruciate retaining knees, as well as posterior stabilized prosthetic knees, either fixed or mobile bearing. Suitable trials for cruciate retaining prostheses are illustrated in FIGS. 1-4 and 8-9; suitable trials for posterior balanced knee prostheses are illustrated in FIGS. 5-7 and 10-11.

Figure 15:
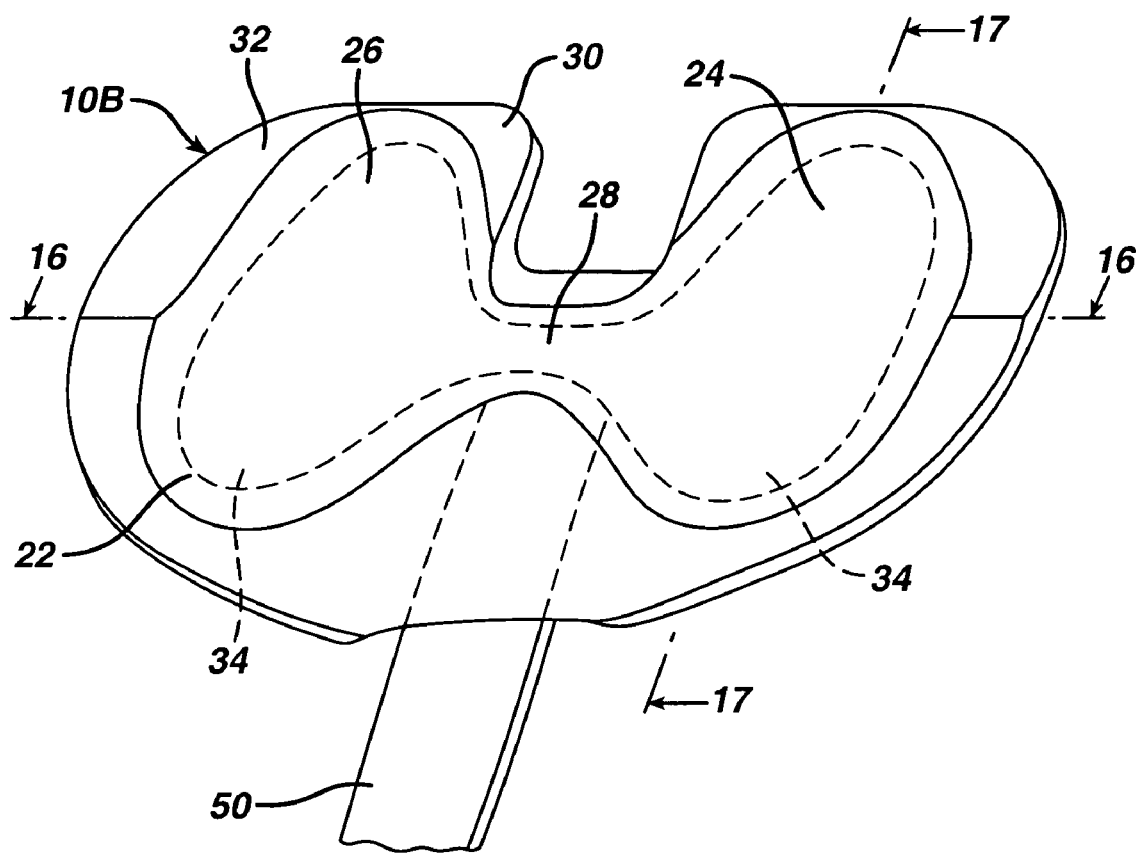
FIG. 15 is a perspective view of a joint tension sensor device incorporating the principles of the present invention.
Figure 16:
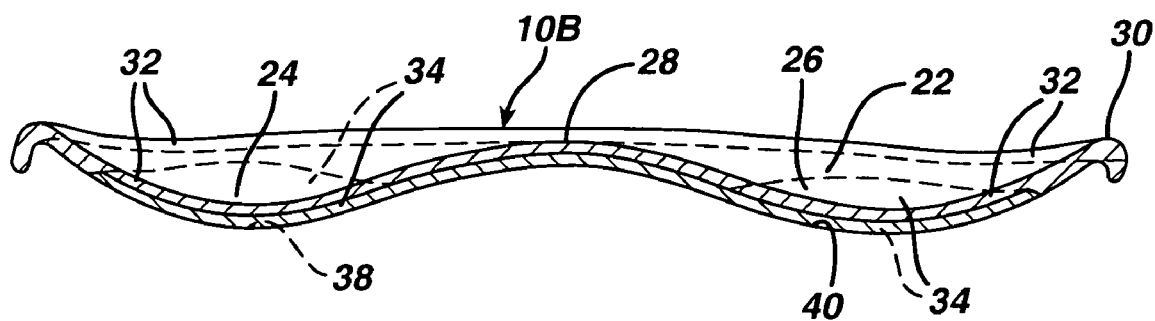
FIG. 16 is a cross-section of the joint tension sensor device of FIG. 15, taken along line 16-16 of FIG. 15.
Figure 17:
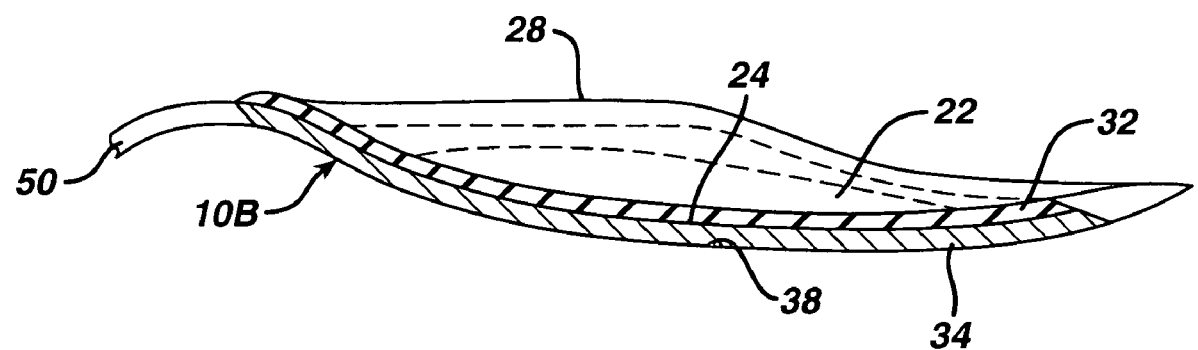
FIG. 17 is a cross-section of the joint tension sensor device of FIGS. 15-16, taken along line 17-17 of FIG. 15.

In addition, in some instances it may be desirable to produce an instrumented tibial trial component where the polymer layer 32 and sensor array 34 are not adhered to the insert body 36. An example of such an alternative design is illustrated in FIGS. 15-17.

The femoral trials 12, 12A (FIGS. 8-11) may be standard commercially available products, made of standard materials. Standard femoral trials are available from DePuy Orthopaedics, Inc. of Warsaw, Ind. However, it should be understood that these commercial products are identified for purposes of illustration only; the invention is not limited to any particular product unless expressly called for in the claims.

All of the trials may be used with commercial prosthetic implants available from DePuy Orthopaedics, Inc. of Warsaw, Ind. However, it should be understood that these commercial products are identified for purposes of illustration only; the invention is not limited to any particular product unless expressly called for in the claims.

A variety of methods may be used to make the illustrated instrumented tibial trial 11. For example, a sheet of polymer material such as high density polyethylene can be placed over the proximal surface 37 of a standard commercially available tibial trial insert body 36, such as a nylon body, heated and vacuum-formed over the trial insert body. During the vacuum forming process, the sheet of polymer material forms over the proximal surface 37 of the trial insert body 36. After the polymer material has cooled, the formed polymer layer 32 is removed from the trial insert body. Excess polymer material may be trimmed away. The resultant polymer layer or cover has curved concave condylar portions on the top side (proximal surface) and curved convex condylar portions on the underside (distal surface).

The proximal surface 37 of the tibial trial insert body 36 can be prepared to receive the sensor array 34 and polymer layer 32 by roughening the surface 37 with fine sandpaper. When the proximal surface 37 has sufficient porosity to form a bond, a silicone adhesive (e.g. E43 ELASTOSIL available from Wacker-Chemie GmbH of Germany) is applied to bond the sensor array 34 to the proximal surface 37 of the tibial trial insert body 36 and to the underside of the preformed polymer layer 32. Since the sensor array 34 is formable and flexible, it becomes contoured in this process, to follow the curved concave contours of the proximal surface 37 of the tibial trial insert body 36 and the curved convex contours of the distal surface of the preformed polymer layer 32. When the composite tibial trial 13 is complete, electrical connectors 50 from the sensor array 34 extend outward beyond the articulating surface 22 of the trial; the electrical connectors 50 are positioned to be easily accessible from the anterior side of the trial during surgery.

The instrumented tibial trial of the present invention may also be made in separate components. As shown in the embodiment of FIGS. 15-17, the sensor array 34 can be adhered to a polymer 32 but maintained separate from the body 36 of the trial. The same sensor array 34 could then be used, for example, with a plurality of different thicknesses of trial insert bodies 36.

The joint trial is sterilized prior to use in surgery. For the instrumented tibial trial insert 10, 10A, 10B, the sterilization process is preferably one that will adequately sterilize the trial 10, 10A, 10B without damaging the sensor array 34, polymer layer 32, body 36 or bonds between these layers. The sterilization process is preferably one that can be used repeatedly without damaging or compromising these layers and the bonds between these layers. One example of a suitable process is the STERRAD® 100S Sterilization System, a low temperature sterilization system available from Advanced Sterilization Products of Irvine, Calif. The cycle in this commercial system comprises evacuation of the sterilization chamber to 400 mTorr, automatic injection and diffusion of 1.8 ml of vaporized $H_2O_2$ and activation of low temperature $H_2O_2$ gas plasma with 400W RF power at 500 mTorr pressure for 17 minutes. During the second half of the cycle, the above steps are repeated. The sterilization chamber is then vented to return it to atmospheric pressure. The sterilization cycle is then complete. This sterilization system has proven to be effective for repeat sterilization of the prosthetic tibial trial described above; it has been used for ten sterilization cycles without compromising the silicone bond or the capacitive properties of the sensors. However, it is expected that other sterilization techniques can be employed, and the present invention should not be interpreted as being limited to a particular sterilization technique unless expressly called for in the claims.

It should be understood that the above-described manufacturing process is provided as an example of one possible method for making the instrumented trial of the present invention. The invention is not limited to this or to any other process unless expressly called for in the claims. Other processes may be used. For example, if the polymer layer is formed over a metal base having a top surface shaped like the trial body articulating surface 37, other forming methods can be used, including methods utilizing higher temperatures.

The use of a separate master for forming the contoured polymer layer may be particularly desirable in the case of designs where vacuum forming is difficult or undesirable. For example, in the case of trials for posterior-stabilized tibial components, it may be desirable to design a master or process that allows for the formation of a polymer layer in the desired shape. The use of a separate master will allow greater flexibility in the choice of materials and methods for forming the polymer layer. It should also be understood that the polymer layer could be made in two or more pieces to protect discrete sensor arrays.

In addition, due to the expense of each sensor array 34, it may be desirable to produce a single or limited number of independent joint tension sensor devices, such as that shown at 10B in FIGS. 15-17. Such a joint tension sensor device can be used with more than one size of tibial trial; for example, such a joint tension sensor device could be designed to be used with two or three close sizes of trials.

Moreover, it may be desirable to use separate sensor elements or arrays that are connected to provide input to the same computer. The term "sensor array" as used herein should be understood to include both integral and separate configurations of sensors and sensor mats unless expressly limited by the claims. "Sensor array" is intended to broadly encompass devices such as those described herein as well as those made of other materials (e.g., a capacitive fabric) and having other characteristics.

In use in arthroplasties, the surgeon performs the initial surgical steps in a standard manner. When the point of trialing is reached, the surgeon uses the instrumented joint trial of the present invention (e.g., tibial trial 13) instead of prior art joint trials, along with a standard complementary prosthetic joint trial (e.g. femoral trial 12, 12A). The electrical connector 50 of the sensor array 34 is hooked up to one end of a lead cord, shown diagrammatically at 52 in FIG. 14, the other end of which is hooked up to a computer, shown diagrammatically at 54 in FIG. 14. The lead cord 52 can be kept sterile in the field by covering it with a clear tube drape. The system may also include a image recorder, shown diagrammatically at 56 in FIG. 14, such as a digital video camera, that is also connected to the computer 54. The computer may be programmed with commercially available software for analysis of the data provided by the instrumented tibial trial; suitable software is available from novel Electronics gmbH under the designation "pliance" ("pliance FTM-KE" software, along with other components such as a "pliance FTM-KE" electronics analyzer, other novel KE software, etc.).

The surgeon then manipulates the patient's leg (or other limb as the case may be), taking the knee through its full range of motion. As the surgeon does so, the articulating distal surface of the femoral trial contacts the articulating proximal surface of the polymer layer of the tibial trial. Depending on the gap between the resected femur and tibia and the size of trials used and the condition of the soft tissue around the joint, there will be forces between the articulating surfaces of the trials. These forces may vary in concentration, position and magnitude with, for example, the position of the knee. The surgeon may concurrently analyze the pressure distribution in each condyle to ensure that pressure is not unduly concentrated in one area, to thereby maximize the longevity of the implant.

From the forces measured and pressure distributions, the surgeon can also determine whether additional bone must be removed, whether soft tissue needs to be released, and whether the size of implant is optimal, for example. A series of small soft tissue releases can be performed, and the surgeon can analyze the effect of each to ensure that the release is not excessive. Data from the sensor array 34 can be recorded simultaneously with video images, so that the surgeon is not limited to "real time" evaluation, but can also review the data after manipulating the knee.

The surgeon may wish to use the prosthetic trials of the present invention in conjunction with standard surgical tensors, particularly those that measure force mechanically. Thus, the output from the sensor array 34 can be calibrated to correlate with the mechanical measurement. The surgeon may also wish to use the prosthetic trials of the present invention together with spacer blocks.

Figure 14:
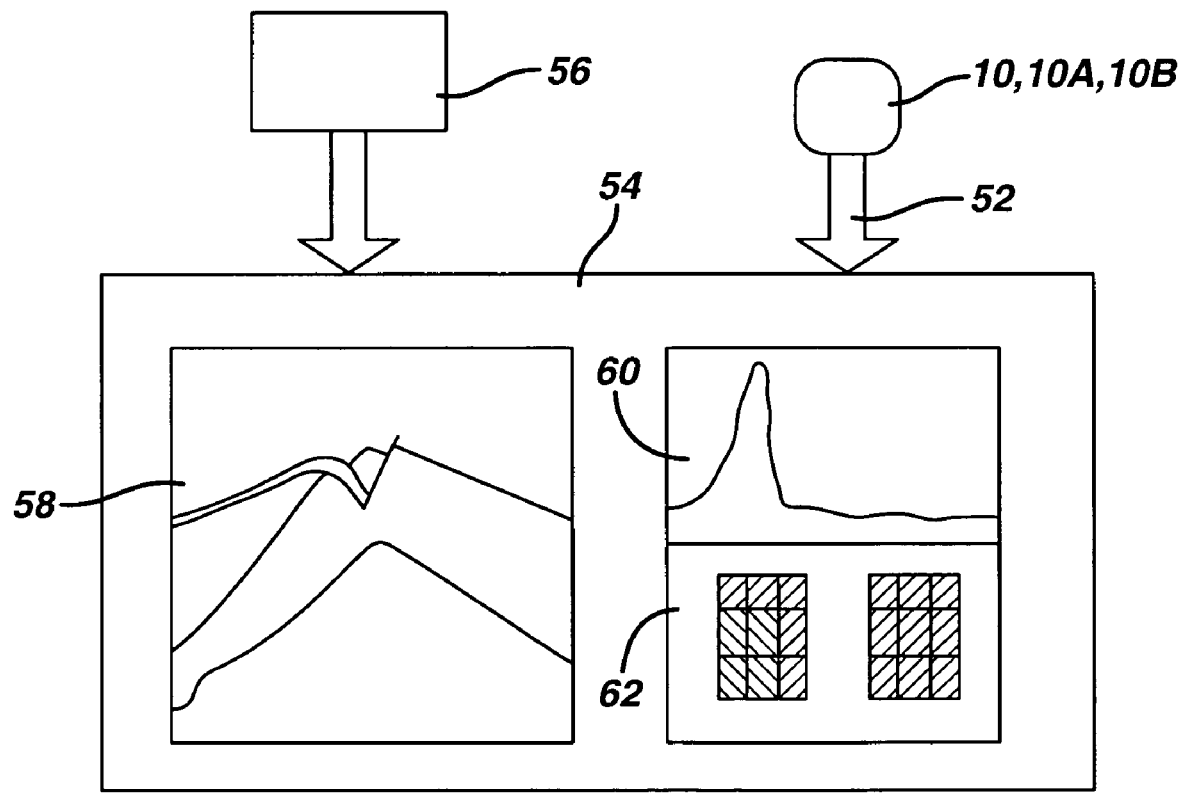
FIG. 14 is a diagrammatic view of a system including the instrumented tibial trial of the present invention, providing input to a computer that also receives input from an image recorder.

The display at the computer 54 may include, for example, a video image, shown diagrammatically at 58 in FIG. 14, a display of the magnitude of force, shown diagrammatically at 60 in FIG. 14, and a display of the concentration of pressure, shown diagrammatically at 62 in FIG. 14. As indicated above, the data can be recorded so that the surgeon is not limited to real time analysis. It should be understood that these displays are identified by way of example only; the present invention is not limited to any particular display or to the use of a computer with such inputs unless expressly called for in the claims.

In cruciate retaining procedures, the surgeon can use the information provided to release the posterior cruciate ligament. The surgeon can balance the posterior cruciate ligament with the trials in place, and can assess balance using objective data.

After the surgeon is satisfied with the flexion and extension gaps, the size and components of the prosthetic implant trial and the balance of forces exerted by the soft tissue surrounding the joint, the surgeon can then select the optimal prosthetic implant components and continue with the surgery in the normal manner.

It will be appreciated that the principles of the present invention can also be applied to the training of surgeons. For example, the system and method of the present invention could be used in learning surgical techniques on cadavers. The system of the present invention may also prove useful in optimizing the designs of implants.

Although the illustrated embodiments of the invention are associated with tibial trials, it should be understood that the femoral trial could alternatively or additionally be the instrumented one. In addition, the device and methods of the present invention could be used on spacer blocks used in the procedure.

Some variations in the above-described components, system and methods may be desirable. For example, the thickness of the prosthetic trial may be adjusted. Instead of the trial body being dimensioned substantially like the corresponding final implant component, the trial body can be made slightly thinner, to account for the thickness of the polymer layer and sensor array. Thus, the body of the trial can be made $\frac{1}{32}$ inch thinner than the implant to account for the thickness of the polymer layer, and can be made an additional 1 mm thinner to account for the thickness of the sensor array; however, it may be desirable for the total insert to be slightly thicker than the reduction in thickness of the trial to insure loading of the insert.

Thus, the present invention provides the surgeon with an apparatus, method, and system for evaluating overall knee balance intraoperatively. It allows the surgeon to assess balance throughout the range of motion of the knee, avoiding flexion, extension and midstance imbalances. It can help the surgeon: understand the influence of implant orientation and soft tissue balance on one another; manage severe deformities with proper releases while avoiding inadvertent over-release; and determine the proper tension in the posterior cruciate ligament for cruciate sparing implants required to obtain adequate stability and kinematics. It can be used to train surgeons to perform these tasks efficiently.

While only specific embodiments of the invention have been described and shown, it is apparent that various alternatives and modifications can be made thereto. Moreover, those skilled in the art will also recognize that certain additions can be made to these embodiments. It is, therefore, the intention in the appended claims to cover all such alternatives, modifications and additions as may fall within the true scope of the invention.

I claim:

1. An instrumented prosthetic knee trial comprising:
   an articulating surface;
   a polymer layer at the articulating surface;
   a body having a curved contoured concave surface, the concave surface being curved in two intersecting planes; and
   a sensor array between the polymer layer and the curved contoured surface of the body, the sensor array having a curved contour including a convex portion and a concave portion, the convex portion and the concave portion both being curved in two intersecting planes, the convex portion contacting and conforming to the shape of at least part of curved contoured concave surface of the body, the sensor array being capable of generating a signal in response to pressure;
   the polymer layer having a curved contour including a convex surface and a concave surface, the convex surface contacting and conforming to the shape of at least part of the concave portion of the sensor array, the convex surface of the polymer layer overlying substantially all of the concave surface of the sensor array;
   wherein the body, sensor array and polymer layer comprise discrete components, the sensor array being adhered to at least one of the convex surface of the polymer layer and the concave surface of the body.

2. The instrumented prosthetic joint trial of claim 1 including a tibial tray trial, wherein the body comprises a tibial insert trial received in the tibial tray trial, said polymer layer and sensor array being carried on the tibial insert trial.

3. The instrumented prosthetic joint trial of claim 1 wherein the polymer layer has a thickness of about 1/32 inch.

4. The instrumented prosthetic joint trial of claim 1 wherein the polymer layer comprises polyethylene.

5. The instrumented prosthetic joint trial of claim 1 wherein the curved contoured surface of the body includes two concave portions, the curved contour of the sensor array includes two convex portions contacting the two concave portions of the body and two concave portions overlying the two convex portions, and the curved contour of the polymer layer includes two convex surfaces contacting the two concave portions of the sensor array and two concave surfaces overlying the two convex surfaces.

6. The instrumented prosthetic joint trial of claim 1 further comprising electrical leads connected to the sensor array and extending beyond the polymer layer.

7. A system for balancing soft tissue intraoperatively during knee joint arthroplasty comprising:
   a first joint trial having a curved convex articulating surface;
   a second joint trial having a curved concave articulating surface for receiving the convex articulating surface of the first joint trial, the curved concave articulating surface of the second joint trial being curved in two intersecting planes;
   the second joint trial including:
      a polymer layer at the articulating surface, the polymer layer having a curved concave top surface and an opposite curved convex surface, the curved concave top surface and the curved convex opposite surface being curved in two intersecting planes;
      a sensor array below the polymer layer and a body below the sensor array, the body defining the curved concave surface of the second joint trial, the sensor array having a curved concave portion contacting and substantially conforming to the curved convex surface of the polymer layer and a curved convex portion contacting and substantially conforming to the curved concave surface of the articulating surface of the body, the sensor array being capable of generating a signal in response to pressure; a body below the sensor array, the body having a curved concave surface adjacent to the sensor array;
   wherein the sensor array, the polymer layer and body comprise discrete components; and
   wherein the sensor array is adhered to at least one of the curved convex surface of the polymer layer and the curved concave surface of the body.

8. The system of claim 7 wherein the first joint trial comprises a femoral trial and the second joint trial comprises a tibial trial.

9. The system of claim 7 wherein the polymer layer has a thickness of about 1/32 inch.

10. The system of claim 7 wherein the polymer layer comprises polyethylene.

11. The system of claim 7 further comprising electrical signal carrying lines leading from the sensor array, at least parts of said electrical signal carrying lines being spaced from the polymer layer.

12. The system of claim 11 further comprising a computer connected to the electrical signal carrying lines.

13. The system of claim 12 further comprising a camera operatively connected to the computer.

14. A method of balancing soft tissue during knee joint arthroplasty comprising:
   providing a first joint trial having a curved convex articular surface;
   providing a second joint trial having a curved concave articular surface for receiving the convex articular surface of the first joint trial, the curved concave articular surface being curved in two intersecting planes;
   the second joint trial including:
      a protective layer at the articulating surface, the protective layer have a concave surface and an opposite convex surface, both the concave surface and the convex surface being curved in two intersecting planes;
      a sensor array below the protective layer, the sensor array having a curved contour substantially conforming to the curved contour of the articulating surface of the second joint trial, the curved contour of the sensor array including a convex surface and an opposite concave surface, the concave surface of the sensor array being curved in two intersecting planes and contacting the convex surface of the protective layer, the convex surface of the protective layer substantially conforming to and substantially covering the concave surface of the sensor array, the sensor array being capable of generating a signal in response to pressure; and
      a body below the sensor array, the body defining the curved concave surface of the second joint trial, the curved concave surface being curved in two intersecting planes, the convex surface of the sensor array contacting the curved concave surface of the body, the body and the protective layer comprising discrete components;
      the sensor array being adhered to at least one of the curved convex surface of the protective layer and the curved concave surface of the body;
   the method further comprising:
   resecting adjacent portions of two bones;
   placing the first joint trial on one of the resected bones and placing the second joint trial on the second resected bone;
   flexing the bones about the first and second joint trials so that the curved convex articular surface of the first joint trial bears against the concave surface of the protective layer of the second joint trial.

15. The method of claim 14 wherein the protective layer comprises polyethylene.

16. The method of claim 14 wherein the protective layer has a thickness of about 1/32 inch.

17. The method of claim 14 further comprising determining the contact area on one concave area of the articulating surface of the second joint trial at a plurality of relative positions of the first and second joint trials.

18. The method of claim 14 further comprising determining the distribution of pressure on one concave area of the articulating surface of the second joint trial at a plurality of relative positions of the first and second joint trials.

19. The method of claim 14 further comprising measuring forces at the articulation between the first and second trials.

20. The method of claim 14 further comprising intraoperatively recording data selected from the group including at least one of the following: images of the surgical procedure; forces at the articulation between the first and second trials; and pressure distribution across at least a portion of the sensor array.

21. The method of claim 14 further comprising releasing soft tissue around the joint.

22. A method of instructing surgeons in the art of knee joint arthroplasty comprising:
   providing a first joint trial having a curved convex articular surface;

providing an instrumented second joint trial having a curved concave articulating surface for receiving the convex articulating surface of the first joint trial, the curved concave articulating surface being curved in two intersecting planes;

the second joint trial including:

a protective layer having a curved concave surface and an opposite convex surface, both the curved concave surface and the convex surface being curved in two intersecting planes;

a sensor array below the protective layer, the sensor array having a curved contour including a convex portion and an opposite concave portion, both the convex portion and the concave portion being curved in two intersecting planes, the sensor array being capable of generating a signal in response to pressure; and a body below the sensor array, the body defining the curved concave surface receiving the convex portion of the sensor array, the curved concave surface of the body being curved in two intersecting planes, the body and the protective layer comprising discrete components;

wherein the sensor array is sandwiched between the body and the protective layer with the convex portion of the sensor array contacting and conforming to the concave surface of the body of the second joint trial and with the convex surface of the protector contacting, conforming to and substantially covering the concave portion of the sensor array; and wherein the sensor array is adhered to at least one of the convex surface of the protective layer and the concave surface of the body;

the method further comprising:

resecting adjacent portions of two bones;

placing the first joint trial on one of the resected bones and placing the second joint trial on the second resected bone;

flexing the bones about the first and second joint trials so that portions of the first joint trial bear against contact portions of the protective layer.

23. The method of claim 22 further comprising providing a computer to receive signals from the sensor array.

24. The method of claim 23 further comprising providing an image recording device operatively connected to the computer.

25. A system for balancing soft tissue intraoperatively during knee joint arthroplasty comprising:

a body having a curved concave surface, the curved concave surface being curved in two intersecting planes;

a conformable sensor array; and a preformed protective cover having a curved concave surface and an opposite curved convex surface, both the curved concave surface and the curved convex surface being curved in two intersecting planes, the convex surface of the preformed protective cover being sized and shaped to correspond to the shape of the curved concave surface of the body;

wherein the body, the sensor array and preformed protective cover comprise discrete components; and wherein the sensor array is adhered to at least one of the body and the protective cover.

26. The system of claim 25 wherein the preformed protective layer is locked to the joint trial and the conformable sensor array is positioned between the curved convex surface of the preformed protective cover and the curved concave surface of the body.

27. The system of claim 26 wherein the protective layer is adhered to the sensor array and to the body.

* * * * *

UNITED STATES PATENT AND TRADEMARK OFFICE
CERTIFICATE OF CORRECTION

PATENT NO. : 7,591,854 B2  
APPLICATION NO. : 10/667763  
DATED : September 22, 2009  
INVENTOR(S) : Ray C. Wasielewski It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1173 days.

Signed and Sealed this

Fourteenth Day of December, 2010

David J. Kappos
*Director of the United States Patent and Trademark Office*